(12) United States Patent
Shudo et al.

(10) Patent No.: US 9,259,454 B2
(45) Date of Patent: Feb. 16, 2016

(54) SOLID COMPOSITION

(75) Inventors: Aiko Shudo, Ichikawa (JP); Shin Koike, Chiba (JP); Nobuteru Ishizuka, Funabashi (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 14/343,608

(22) PCT Filed: Sep. 14, 2012

(86) PCT No.: PCT/JP2012/073645
§ 371 (c)(1),
(2), (4) Date: Mar. 7, 2014

(87) PCT Pub. No.: WO2013/039211
PCT Pub. Date: Mar. 21, 2013

(65) Prior Publication Data
US 2014/0213503 A1 Jul. 31, 2014

(30) Foreign Application Priority Data

Sep. 16, 2011 (JP) .................................. 2011-202616
Nov. 1, 2011 (JP) .................................. 2011-240243

(51) Int. Cl.

| | |
|---|---|
| *A61K 38/16* | (2006.01) |
| *A23L 1/305* | (2006.01) |
| *A23G 3/44* | (2006.01) |
| *A23L 1/236* | (2006.01) |
| *A61K 9/00* | (2006.01) |
| *A61K 47/26* | (2006.01) |

(52) U.S. Cl.
CPC ................ *A61K 38/168* (2013.01); *A23G 3/44* (2013.01); *A23L 1/2364* (2013.01); *A23L 1/3055* (2013.01); *A61K 9/0056* (2013.01); *A61K 47/26* (2013.01); *A23V 2002/00* (2013.01)

(58) Field of Classification Search
USPC ........................................................ 426/548
See application file for complete search history.

(56) References Cited

U.S. PATENT DOCUMENTS

| 5,789,380 | A | 8/1998 | Miyazaki et al. |
| 6,740,339 | B1 * | 5/2004 | Ohkouchi et al. ............. 424/464 |
| 2008/0213339 | A1 * | 9/2008 | Imboden et al. ............. 424/436 |
| 2011/0052732 | A1 * | 3/2011 | Ueda ............................. 424/729 |
| 2013/0156923 | A1 | 6/2013 | Shudo et al. |

FOREIGN PATENT DOCUMENTS

| CN | 101983072 A | 3/2011 |
| CN | 102711832 A | 10/2012 |
| JP | 2007 106683 | 4/2007 |
| JP | 3999825 | 10/2007 |
| JP | 2010 150212 | 7/2010 |
| JP | 2010 173962 | 8/2010 |
| WO | 03/020241 A2 | 3/2003 |

OTHER PUBLICATIONS

Kikkoman Shoyu Co Ltd—JP 51073113—Derwent Abstract (Jun. 24, 1976).*
Aiso et al., "Short- and Long-Term Intake of Wheat Albumin Affects Blood Glucose and HbA1c Levels in Healthy and Type 2 Diabetic Subjects"—Clinical and Experimental Pharmacology and Physiology (2007), 34, S90-S92.*
Miyazaki, T., et al., "Shelf Life of Drink and Powdered Soup Containing Wheat Albumin", The Japanese Journal of Nutrition, vol. 57, No. 4, pp. 221-227, (1999) (with English abstract).
"Effects of Single Administration of Wheat Albumin by Hard Capsules on Blood Glucose Control", Japanese Phalmacology & Therapeutics, vol. 36, No. 8, pp. 761-765, (2008) (with English abstract and computer generated translation).
Kodama, T., et al., "Effects of single and long-term administration of wheat albumin on blood glucose control: randomized controlled clinical trials", European Jounal of Clinical Nutrition, vol. 59, pp. 384-392, (2005).
International Search Report Issued Oct. 30, 2012 in PCT/JP12/073645 Filed Sep. 14, 2012.
Rong Zhi-mei, "A New Product of Biological Industry and Instructions on Development of New Technology", (Shengwu Huagong Xinchanpin Yu Xinjishu Kaifa Zhinan), $2^{nd}$ Edition, Chemical Industry Press, Apr. 2004, pp. 310-311 (with partial English translation).
Zhao Cun-mei, et al., "Technology of Effervescent Agent", Chemical Industry Press, Jan. 2007, pp. 2, (with partial English translation).
Yulong Zheng, "Guidance for Understanding Food Label", Published by China Population Publishing House, Apr. 2013, Publication No. 013332, 4 pp. (with partial English Translation).

* cited by examiner

*Primary Examiner* — Elizabeth Gwartney
(74) *Attorney, Agent, or Firm* — Oblon, McClelland, Maier & Neustadt, L.L.P.

(57) ABSTRACT

The present invention provides a solid composition comprising the following ingredients (A) and (B):
  (A) wheat albumin, and
  (B) a C6 to C12 sugar alcohol,
wherein a content mass ratio of the ingredient (B) to the ingredient (A), (B)/(A), is 0.2 or higher.

16 Claims, No Drawings

US 9,259,454 B2

SOLID COMPOSITION

FIELD OF THE INVENTION

The present invention relates to a solid composition comprising wheat albumin.

BACKGROUND OF THE INVENTION

In recent years, a considerably increased number of patients suffer glucose metabolism disorders including obesity and Type II diabetes (hyperglycemia), mainly due to a change in dietary habits.

Generally, blood glucose level elevates after a meal, particularly after ingestion of a meal containing carbohydrate, and insulin is secreted by pancreatic β cells. Insulin acts on muscle, liver, adipose tissue, and the like and promotes the intake of sugar into cells, whereby an acute increase in blood glucose level after a meal is suppressed. However, when the postprandial blood glucose level remains high due to impaired insulin sensitivity (i.e., insulin resistance), the pancreas secrets a large amount of insulin so as to suppress an increase in blood glucose. If such a state continues for a long period of time, the pancreas is exhausted, to thereby decrease insulin secretion by pancreatic β cells. Eventually, the insulin action mechanism does not normally function, which triggers Type II diabetes or the like.

Postprandial hyperglycemia caused by insulin resistance is also observed in non-diabetes healthy people and borderline diabetes patients. In addition, postprandial hyperglycemia is known to cause obesity, hyperlipidemia, arteriosclerosis, etc. as well as Type II diabetes, and to serve as an exacerbation factor therefor. Therefore, prevention of postprandial hyperglycemia is very important from the viewpoints of health maintenance, lowering the risk for onset of these symptoms and disorders, and prevention thereof.

Under such circumstances, in recent years, there have been developed a number of substances that can suppress an acute increase in postprandial blood glucose and insulin secretion. Some of these substances are amylase inhibitors, and a wheat-originating amylase inhibitor is employed for prevention and treatment of diabetes, obesity, etc. (Non-Patent Document 1).

The endosperm of wheat contains about 10 to about 15% protein, and albumin (water-soluble protein) occupies about 11% of the protein composition. It has been reported that albumin has α-amylase inhibitory activity and physiological functions such as postprandial blood glucose increase inhibitory action and insulin resistance improving action (Non-Patent Documents 1 and 2). Above all, a wheat albumin having an electrophoretic mobility of 0.19 exhibits high α-amylase inhibitory activity, and therefore application thereof to various foods is expected.

In order to obtain physiological functions of wheat albumin, a single injection of the wheat albumin having an electrophoretic mobility of 0.19 (hereinafter may be referred also to as "0.19 wheat albumin") in an amount of 125 mg or more per single diet is believed effective (Non-Patent Document 2). Hitherto, as commercial health foods containing an effective amount of wheat albumin, soup and hard capsules are available on the market. Also, Patent Document 1 discloses a tablet containing 0.19 wheat albumin.

CITATION LIST

Patent Documents

Patent Document 1: JP-A-2010-173962

Non-Patent Documents

Non-Patent Document 1: Japanese Pharmacology & Therapeutics, 2008, Vol. 36, No. 8, p. 761-765
Non-Patent Document 2: European Journal of Clinical Nutrition, 2005, Vol. 59, p. 384-392

SUMMARY OF THE INVENTION

The present invention provides a solid composition comprising the following ingredients (A) and (B):
 (A) wheat albumin, and
 (B) a C6 to C12 sugar alcohol,
 wherein the content mass ratio of ingredient (B) to ingredient (A), (B)/(A), is 0.2 or higher.

DETAILED DESCRIPTION OF THE INVENTION

In order to easily take wheat albumin for a long period of time, a wheat albumin solid composition, which can be easily taken at a small single dose at a time, is advantageously employed.

However, studies by the present inventors revealed that difficulty is encountered in blending a wheat albumin into a solid composition at such a high concentration that the effective amount can be taken by a small single dose. In other words, it is revealed that when the wheat albumin concentration increases, an offensive odor attributed to wheat albumin is generated, which makes eating difficult. In addition, at a high wheat albumin concentration, bad returning odor remains. Here, the term "bad returning odor" refers to an odor returning from the gullet during and/or after ingestion of wheat albumin.

Thus, the present invention relates to provision of a solid composition excellent in taste and flavor, which reduces an offensive odor and bad returning odor, even the composition has a high wheat albumin concentration. Notably, Patent Document 1 is silent about reduction of an offensive odor or the like of a tablet containing wheat albumin.

The present inventors conducted extensive studies to solve the aforementioned problem, and found that, through incorporation of a sugar alcohol, particularly a specific sugar alcohol, into a solid composition, regardless of a high wheat albumin concentration, an offensive odor intrinsic to wheat albumin and bad returning odor occurring during and/or after ingestion can be reduced, and the flavor and taste of the solid composition can be enhanced.

The present invention enables provision of a solid composition excellent in taste and flavor which reduces an offensive odor derived from wheat albumin during injection and bad returning odor occurring during and/or after ingestion, even though the composition has a high wheat albumin concentration.

The solid composition of the present invention ensures, at a small single dose, ingestion of wheat albumin in such an amount that the physiological effect of wheat albumin can be attained. Thus, the effect of wheat albumin can be sufficiently expected for a long period of time.

The wheat albumin (A) employed in the present invention is a water-soluble protein belonging to the albumin family derived from the endosperm of wheat. For attaining high α-amylase inhibitory activity, wheat albumin preferably contains a wheat albumin having an electrophoretic mobility of 0.19. As used herein, the term "electrophoretic mobility" refers to a mobility of a sample subjected to polyacrylamide gel electrophoresis according to the method of Davis (Annals of the New York Academy of Science, 121, 404-427, 1964).

The aforementioned wheat albumin may be obtained through extraction from the endosperm of wheat. The method of extracting wheat albumin from wheat employed in the present invention is, for example, a method for preparing an amylase inhibitor disclosed in JP-A-9-172999.

Alternatively, commercial products such as Wheat Albumin NA-1 (product of Nisshin Pharma Inc.) may also be used.

The content of wheat albumin (A) in the solid composition of the present invention is preferably 10 mass % (hereinafter may be referred to simply as "%") or higher, more preferably 20% or higher, even more preferably 30% or higher, from the viewpoints of the ingestion amount for effectively attaining the physiological effect and an ingestion form capable of a single ingestion at small dose. From the viewpoints of reduction in an offensive odor intrinsic to wheat albumin and bad returning odor, the content of wheat albumin (A) is preferably 70% or lower, more preferably 60% or lower, even more preferably 55% or lower, even more preferably 50% or lower. More specifically, the content of wheat albumin (A) is preferably 10 to 70%, more preferably 20 to 70%, even more preferably 30 to 60%, even more preferably 30 to 55%, even more preferably 30 to 50%.

The content of 0.19 wheat albumin (a) in the wheat albumin (A) is preferably 10% or higher, more preferably 15% or higher, even more preferably 20% or higher, even more preferably 25% or higher, from the viewpoints of the ingestion amount for effectively attaining the physiological effect. From the viewpoint of ease of wheat albumin production, the content of 0.19 wheat albumin (a) is preferably 60% or lower, more preferably 40% or lower, even more preferably 35% or lower, even more preferably 31% or lower. More specifically, the content of 0.19 wheat albumin (a) is preferably 10 to 60%, more preferably 15 to 40%, even more preferably 20 to 35%, even more preferably 25 to 31%.

The content of 0.19 wheat albumin (a) in the solid composition of the present invention is preferably 6% or higher, more preferably 7% or higher, even more preferably 7.5% or higher, from the viewpoint of the ingestion amount for ensuring physiological effects. From the viewpoint of reduction of an offensive odor intrinsic to wheat albumin and bad returning odor, the content of 0.19 wheat albumin (a) in the solid composition is preferably 18% or lower, more preferably 15% or lower, even more preferably 13% or lower. More specifically, the content of 0.19 wheat albumin (a) in the solid composition is preferably 7 to 18%, more preferably 7 to 15%, even more preferably 7.5 to 13%.

The content of 0.19 wheat albumin in the solid composition of the present invention may be determined through HPLC. For example, a method for determining a content of 0.19 amylase inhibitor disclosed in JP-A-9-172999 may be employed.

Examples of C6 to C12 sugar alcohol (B) employed in the present invention include maltitol, sorbitol, lactitol and the like. These sugar alcohols may be used singly or in combination of two or more species.

Of these, from the viewpoints of reduction in an offensive odor intrinsic to wheat albumin and bad returning odor, at least one species selected from among maltitol, sorbitol, and lactitol is preferred, with maltitol, sorbitol, or a combination thereof being more preferred. Among them, maltitol is even more preferred. The sugar alcohols may be anhydrous or hydrated.

The content of C6 to C12 sugar alcohol (B) in the solid composition of the present invention is preferably 10% or higher, more preferably 20% or higher, even more preferably 30% or higher, even more preferably 35% or higher, from the viewpoint of reduction of an offensive odor intrinsic to wheat albumin and bad returning odor. From the viewpoint of inclusion of wheat albumin showing effectively physiological effects, the content of C6 to C12 sugar alcohol (B) in the solid composition is preferably 90% or lower, more preferably 65% or lower, even more preferably 60% or lower, even more preferably 55% or lower. More specifically, the content of C6 to C12 sugar alcohol (B) in the solid composition is preferably 10 to 90%, more preferably 20 to 65%, even more preferably 30 to 60%, even more preferably 35 to 55%.

The sugar alcohol content may be determined through HPLC. For example, the sugar alcohol content may be determined through differential refractometry by means of an amino column (*Shokumotsu seni, kiso to ohyo* (Dietary Fiber, its Basis and Application) supervised by Japanese Association for Dietary Fiber Research, edited by Editorial Committee of Japanese Association for Dietary Fiber Research, authored by Seiichiro Aoki et al., published by Dai-Ichi Shuppan Co., Ltd., October 2008).

In the solid composition of the present invention, it is important to adjust the content mass ratio of C6 to C12 sugar alcohol (B) to wheat albumin (A), (B)/(A), to 0.2 or higher. Through adjusting the proportion of sugar alcohol (B) to 0.2 or higher based on 1 of wheat albumin (A), an offensive odor intrinsic to wheat albumin and bad returning odor can be reduced.

From the same viewpoint, the content mass ratio of C6 to C12 sugar alcohol (B) to wheat albumin (A), (B)/(A), is preferably 0.2 or higher, more preferably 0.4 or higher, even more preferably 0.5 or higher, even more preferably 0.7 or higher. From the viewpoint of inclusion of 0.19 wheat albumin for ensuring physiological effects, the ratio (B)/(A) is preferably 10 or lower, more preferably 7 or lower, even more preferably 5 or lower, even more preferably 2 or lower, even more preferably 1.9 or lower. More specifically, the ratio (B)/(A) is preferably 0.2 to 10, more preferably 0.4 to 7, even more preferably 0.4 to 5, even more preferably 0.5 to 2, even more preferably 0.7 to 1.9.

In the solid composition of the present invention, the content mass ratio of C6 to C12 sugar alcohol (B) to 0.19 wheat albumin (a), (B)/(a), is preferably 0.8 or higher. Through adjusting the proportion of sugar alcohol (B) to 0.8 or higher based on 1 of 0.19 wheat albumin (a), an offensive odor intrinsic to wheat albumin and bad returning odor can be reduced.

From the same viewpoint, the content mass ratio of C6 to C12 sugar alcohol (B) to 0.19 wheat albumin (a), (B)/(a), is preferably 0.8 or higher, more preferably 1.5 or higher, even more preferably 2.5 or higher. From the viewpoint of inclusion of wheat albumin for ensuring physiological effects, the ratio (B)/(a) is preferably 10 or lower, more preferably 7.5 or lower. More specifically, the ratio (B)/(a) is preferably 0.8 to 10, more preferably 1.5 to 10, even more preferably 1.5 to 7.5, even more preferably 2.5 to 7.5.

Preferably, the solid composition of the present invention further contains aspartic acid or a salt thereof (C), since not only an offensive odor but also a bad taste intrinsic to wheat albumin can be reduced.

Examples of the salt of aspartic acid (aspartate salt) employed in the present invention include acid addition salts with an inorganic acid such as hydrochloric acid, hydrobromic acid, sulfuric acid, phosphoric acid, or nitric acid; acid addition salts with an organic acid such as acetic acid, propionic acid, succinic acid, glycolic acid, lactic acid, malic acid, tartaric acid, citric acid, maleic acid, fumaric acid, methanesulfonic acid, benzenesulfonic acid, p-toluenesulfonic acid, or ascorbic acid; salts with an inorganic base such as an alkali metal (e.g., sodium, potassium or the like), an alkaline earth metal (e.g., calcium or the like), or ammonium; and salts with an organic base such as an amine (e.g., methylamine, diethylamine, tirethylamine, ethylenediamine or the like) or an alkanolamine (e.g., monoethanolamine, diethanolamine, triethanolamine or the like). Of these, alkali metal salts are preferred.

From the viewpoint of reduction in a bad taste and offensive odor of wheat albumin, the solid composition of the present invention preferably has the content of aspartic acid or a salt thereof (C), in terms of aspartic acid, of preferably 0.005% or higher, more preferably 0.008% or higher, even more preferably 0.01% or higher, even more preferably 0.012% or higher. From the viewpoint of a well-balanced taste and flavor, the content of aspartic acid or a salt thereof is preferably 1% or lower, more preferably 0.8% or lower, even more preferably 0.5% or lower, even more preferably 0.1% or lower, even more preferably 0.05% or lower, even more preferably 0.025% or lower, even more preferably 0.02% or lower. More specifically, the content of aspartic acid or a salt thereof is preferably 0.005% to 1%, more preferably 0.008 to 0.8%, even more preferably 0.01 to 0.5%, even more preferably 0.01 to 0.1%, even more preferably 0.01 to 0.05%, even more preferably 0.01 to 0.02%.

In the present invention, the content of aspartic acid or a salt thereof (C) includes not only that of aspartic acid or a salt thereof incorporated into the composition but also that originating from wheat albumin and other raw materials.

From the viewpoint of reduction in a bad taste and offensive odor intrinsic to wheat albumin, the solid composition of the present invention preferably has a content mass ratio of 0.19 wheat albumin (a) to aspartic acid or a salt thereof (c), (a)/(c), in terms of aspartic acid, of 1,000 or lower, more preferably 910 or lower, even more preferably 900 or lower, even more preferably 850 or lower, even more preferably 780 or lower, even more preferably 750 or lower. From the viewpoints of suppression of the taste of aspartic acid or a salt thereof and realization of a well-balanced taste and flavor, the ratio (a)/(c) is preferably 10 or higher, more preferably 15 or higher, even more preferably 50 or higher, even more preferably 100 or higher, even more preferably 200 or higher, even more preferably 400 or higher, even more preferably 500 or higher. More specifically, the content mass ratio of 0.19 wheat albumin (a) to aspartic acid or a salt thereof (C), (a)/(c), in terms of aspartic acid, is preferably 10 to 1,000, more preferably 15 to 910, even more preferably 50 to 900, even more preferably 100 to 850, even more preferably 200 to 780, even more preferably 500 to 750.

In addition to the aforementioned ingredients, the solid composition of the present invention preferably contains a carbonate salt (D) and an organic acid (E). Through combination of wheat albumin with a carbonate salt and an organic acid, to thereby generate carbonate gas, stickiness and adhesion in the mouth can be suppressed, and a bad taste intrinsic to wheat albumin can be reduced, even at high wheat albumin concentration. As a result, a solid composition having a favorable texture, taste and flavor can be produced.

Examples of the carbonate salt (D) employed in the present invention include sodium carbonate, sodium hydrogencarbonate, potassium carbonate, potassium hydrogencarbonate, calcium carbonate, magnesium carbonate, sodium sesquicarbonate and the like. These carbonate salts may be used singly or in combination of two or more species.

The solid composition of the present invention preferably has the content of carbonate salt (D) of preferably 2% or higher, more preferably 3% or higher, even more preferably 10% or higher, from the viewpoint of physical properties. From the viewpoint of the taste and flavor, the content of carbonate salt (D) is preferably is 20% or lower, more preferably 19.5% or lower, even more preferably 14% or lower. More specifically, the content of carbonate salt (D) is preferably 2 to 20%, more preferably 3 to 19.5%, even more preferably 10 to 14%.

As the organic acid (E) employed in the present invention, an edible acid may be used. Examples of such an edible organic acid include citric acid, phosphoric acid, succinic acid, ascorbic acid, acetic acid, gluconic acid, malic acid, tartaric acid, fumaric acid, adipic acid and the like. These acids may be used singly or in combination of two or more species. Of these, citric acid and malic acid are preferred from viewpoints of reduced stickiness and adhesion in the mouth during ingestion and excellent mouth feel of bubbles generated. Of these, citric acid is more preferred.

The solid composition of the present invention preferably has the content of organic acid (E) of preferably 2% or higher, more preferably 2.5% or higher, even more preferably 3% or higher, even more preferably 8% or higher, from the viewpoint of physical properties. From the viewpoint of the taste and flavor, the content of organic acid (E) is preferably is 18% or lower, more preferably 15% or lower, even more preferably 12% or lower, even more preferably 11% or lower. More specifically, the content of organic acid (E) is preferably 2 to 18%, more preferably 2.5 to 15%, even more preferably 3 to 12%, even more preferably 8 to 11%.

The solid composition of the present invention preferably has a content mass ratio of wheat albumin (A) to carbonate salt (D), (A)/(D), of 1.5 or higher, more preferably 2.5 or higher, even more preferably 2.6 or higher, even more preferably 3.5 or higher, since stickiness and adhesion in the mouth during ingestion can be suppressed, and a bad taste intrinsic to wheat albumin can be reduced. From the viewpoint of the taste and flavor, the ratio (A)/(D) is preferably 16.5 or lower, more preferably 15.5 or lower, even more preferably 12 or lower, even more preferably 5 or lower. More specifically, the ratio (A)/(D) is preferably 1.5 to 16.5, more preferably 2.5 to 15.5, even more preferably 2.6 to 12, even more preferably 3.5 to 5.

The solid composition of the present invention preferably has a content mass ratio of 0.19 wheat albumin (a) to carbonate salt (D), (a)/(D) of 0.2 or higher, more preferably 0.3 or higher, even more preferably 0.35 or higher, and of 4.1 or lower, more preferably 3.8 or lower, even more preferably 3 or lower, since stickiness and adhesion in the mouth during ingestion can be suppressed, and a bad taste intrinsic to wheat albumin can be reduced. More specifically, the ratio (a)/(D) is preferably 0.2 to 4.1, more preferably 0.3 to 3.8, even more preferably 0.35 to 3.

In the solid composition of the present invention, the equivalent ratio of organic acid (E) to carbonate salt (D) is preferably 0.7 or higher, more preferably 0.8 or higher, even more preferably 0.85 or higher, even more preferably 0.9 or higher, and preferably 1.9 or lower, more preferably 1.8 or lower, even more preferably 1.2 or lower, even more preferably 1.1 or lower, since a harshness attributed to the carbonate salt and an acidic taste of the organic acid are not prominent, to thereby attain a well-balanced taste and flavor. More specifically, the equivalent ratio is preferably 0.8 to 1.8, more preferably 0.85 to 1.2, even more preferably 0.9 to 1.1.

In the present invention, the term "equivalent ratio" refers to a value obtained by dividing the equivalent of organic acid (E) by that of carbonate salt (D) contained in the solid composition.

So long as the effects of the present invention are not impaired, the solid composition of the present invention may appropriately contain, in addition to the aforementioned ingredients, a mineral (e.g., calcium, magnesium, iron, zinc, chromium, selenium, manganese, molybdenum, copper, iodine, phosphorus, potassium, or sodium), a vitamin (e.g., vitamin A, vitamin B1, vitamin B2, vitamin B6, vitamin B12, vitamin C, vitamin E, folic acid, a salt thereof, or an ester of any of these), a sweetener (e.g., a monosaccharide such as fructose, glucose, galactose, xylose, or tagatose; an oligosaccharide such as sucrose, lactose, maltose, trehalose, isomalto-oliogsaccharide, galacto-oliogsaccharide, fructo-oliogsaccharide, lacto-oliogsaccharide, soybean-oliogsaccharide, isomaltulose, or coupling sugar; a sugar alcohol other than C6 to C12 sugar alcohols; or a synthetic sweetener such as saccharin, sucralose, or acesulfame potassium), an acidulant (e.g., citric acid, malic acid, tartaric acid, lactic acid, succinic acid, adipic acid, glucono-δ-lactone, gluconic acid, acetic acid, or fumaric acid), a perfume, a colorant, a preservative, etc.

No particular limitation is imposed on the form of the solid composition of the present invention, so long as the composition is solid at, for example, room temperature (15 to 25° C.). Examples of the composition form include a capsule, a granule, a powder, a tablet, and a pill. Among them, a tablet is preferred, since the effective amount can be taken by a small single dose. To facilitate ingestion, a chewable tablet is more preferred.

In the case where the solid composition of the present invention contains a carbonate salt (D) and an organic acid (E), the solid composition generates carbonate gas in the mouth or in the presence of water.

A composition of such a form may be prepared by appropriately combining any of the following optional additives, according to need: an excipient such as lactose, starch, crystalline cellulose, cane sugar, light anhydrous silicic acid, or calcium hydrogenphosphate; a binder such as hydroxypropylmethylcellulose, hydroxypropylcellulose, gelatin, pregelatinized starch, polyvinylpyrrolidine, polyvinyl alcohol, pullulan, methylcellulose, or hydrogenated oil; a disintegrant such as carmellose, carmellose calcium, croscarmellose sodium, crospovidone, cornstarch, or low-substituted hydroxypropylcellulose; a lubricant such as calcium stearate, magnesium stearate, stearyl sodium fumarate, talc, or silicon dioxide; a corrigent such as stevia or aspartame; a perfume; a bulking filler; a surfactant; a dispersant; a buffer; a preservative; a coating agent; and a carrier such as a diluent.

No particular limitation is imposed on the method for producing the solid composition of the present invention, and the composition is produced through a conventional method. For example, the composition is produced by preparing a mixture of wheat albumin (A), a C6 to C12 sugar alcohol (B), and optional additives and subjecting the mixture to compression molding.

In the case of tablet production, a raw material may be directly compressed and molded (i.e., direct powder compression process), or a raw material may be granulated through dry granulation, wet granulation, or a similar technique, followed by compressing the granules and mold (i.e., granule compression process). From the viewpoint of simplicity, a tablet is preferably formed through direct powder compression process.

In the case of direct compression process, tablets are produced by means of a tableting machine generally employed in the art, such as a rotary tablet press or a single punch tableting machine.

In one case of granulation and compression, a raw material is granulated through extrusion granulation by means of a basket granulator, a spheronization machine, a pelleter, or the like; crush granulation by means of a speed mill, a power mill, or the like; oscillating granulation; agitation granulation; fluidized bed granulation, or a similar technique. The granulated product is dried and sized, and the thus-obtained product is compressed by means of the aforementioned tableting machine, to thereby form tablets. The granulated product preferably has a particle size of 45 μm to 850 μm, more preferably 100 μm to 500 μm.

The tablet form may be circular, or may have an anisotropic shape such as an oval, an ellipse, or a rectangle.

The compression molding pressure during tableting is about 100 to about 3,000 kg/cm$^2$, from the viewpoint of properties of the molded products such as hardness maintenance and disintegration property.

The tablet of the present invention preferably has a weight of 0.1 to 2 g, more preferably 1 to 2 g per tablet, from the viewpoints of easy taking and effectiveness.

As described in the Example hereinbelow, an offensive odor intrinsic to and returning odor attributable to wheat albumin were masked by a C6 to C12 sugar alcohol. Therefore, the C6 to C12 sugar alcohol may be used as a useful agent for masking wheat albumin odor. Among sugar alcohols, at least one member among maltitol, sorbitol, and lactitol is preferred, with maltitol, sorbitol, or a combination thereof being more preferred. Maltitol is even more preferred.

Specific embodiments of the present invention include the compositions, methods, and uses, as disclosed hereinbelow.

<1> A solid composition comprising the following ingredients (A) and (B):
  (A) wheat albumin, and
  (B) a C6 to C12 sugar alcohol, wherein a content mass ratio of the ingredient (B) to the ingredient (A), (B)/(A), is 0.2 or higher.

<2> The solid composition as described in <1> above, which has a content of wheat albumin (A) of 10 mass % or higher, preferably 20 mass % or higher, more preferably 30 mass % or higher, and 70 mass % or lower, preferably 60 mass % or lower, more preferably 55 mass % or lower, even more preferably 50 mass % or lower.

<3> The solid composition as described in <1> or <2> above, which has a content mass ratio of C6 to C12 sugar alcohol (B) to wheat albumin (A), (B)/(A), of 0.2 or higher, preferably 0.4 or higher, more preferably 0.5 or higher, even more preferably 0.7 or higher, and 10 or lower, preferably 7 or lower, more preferably 5 or lower, even more preferably 2 or lower, even more preferably 1.9 or lower.

<4> The solid composition as described in any one of <1> to <3> above, wherein the wheat albumin (A) comprises 0.19 wheat albumin (a), and the wheat albumin (A) has a content of 0.19 wheat albumin (a) of 10 mass % or higher, preferably 15 mass % or higher, more preferably 20 mass % or higher, even more preferably 25 mass % or higher, and 60 mass % or lower, preferably 40 mass % or lower, more preferably 35 mass % or lower, even more preferably 31 mass % or lower.

<5> The solid composition comprising the following ingredients (a) and (B):
(a) 0.19 wheat albumin, and
(B) a C6 to C12 sugar alcohol, wherein a content mass ratio of the ingredient (B) to the ingredient (a), (B)/(a), is 0.8 or higher.

<6> The solid composition as described in any one of <1> to <5> above, which has a content of 0.19 wheat albumin (a) of 6 mass % or higher, more preferably 7 mass % or higher, even more preferably 7.5 mass % or higher, and 18 mass % or lower, more preferably 15 mass % or lower, even more preferably 13 mass % or lower.

<7> The solid composition as described in any one of <1> to <6> above, wherein the C6 to C12 sugar alcohol (B) is at least one species selected from among maltitol, sorbitol, and lactitol, preferably at least one species selected from among maltitol, sorbitol, and lactitol, more preferably maltitol, sorbitol, or a combination thereof, even more preferably maltitol.

<8> The solid composition as described in any one of <1> to <7> above, which has a content of C6 to C12 sugar alcohol (B) of 10 mass % or higher, preferably 20 mass % or higher, more preferably 30 mass % or higher, even more preferably 35 mass % or higher, and 90 mass % or lower, preferably 65 mass % or lower, more preferably 60 mass % or lower, even more preferably 55 mass % or lower.

<9> The solid composition as described in any one of <1> to <8> above, which has a content mass ratio of C6 to C12 sugar alcohol (B) to 0.19 wheat albumin (a), (B)/(a), of 0.8 or higher, more preferably 1.5 or higher, even more preferably 2.5 or higher, and 10 or lower, preferably 7.5 or lower.

<10> The solid composition as described in any one of <1> to <9> above, which further comprises an aspartic acid or a salt thereof (C).

<11> The solid composition as described in <10> above, which has a content of aspartic acid or a salt thereof (C), in terms of aspartic acid, of 0.005 mass % or higher, more preferably 0.008 mass % or higher, even more preferably 0.01 mass % or higher, even more preferably 0.012 mass % or higher, and 1 mass % or lower, preferably 0.8 mass % or lower, more preferably 0.5 mass % or lower, even more preferably 0.1 mass % or lower, even more preferably 0.05 mass % or lower, even more preferably 0.025 mass % or lower, even more preferably 0.02 mass % or lower.

<12> The solid composition as described in <10> or <11> above, which has a content mass ratio of 0.19 wheat albumin (a) to aspartic acid or a salt thereof (c), in terms of aspartic acid, (a)/(c), of 1,000 or lower, preferably 910 or lower, more preferably 900 or lower, even more preferably 850 or lower, even more preferably 780 or lower, even more preferably 750 or lower, and 10 or higher, preferably 15 or higher, more preferably 50 or higher, even more preferably 100 or higher, even more preferably 200 or higher, even more preferably 400 or higher, even more preferably 500 or higher.

<13> The solid composition as described in any one of <1> to <12> above, which further comprises a carbonate salt (D) and an organic acid (E).

<14> The solid composition as described in <13> above, wherein the carbonate salt (D) is at least one species selected from among sodium carbonate, sodium hydrogencarbonate, potassium carbonate, potassium hydrogencarbonate, calcium carbonate, magnesium carbonate, and sodium sesquicarbonate.

<15> The solid composition as described in <13> or <14> above, wherein the organic acid (E) is at least one species selected from among citric acid, phosphoric acid, succinic acid, ascorbic acid, acetic acid, gluconic acid, malic acid, tartaric acid, fumaric acid, and adipic acid, preferably citric acid, malic acid, or a combination thereof, more preferably citric acid.

<16> The solid composition as described in any one of <13> to <15> above, which has a content of carbonate salt (D) of 2 mass % or higher, preferably 3 mass % or higher, more preferably 10 mass % or higher, and 20 mass % or lower, preferably 19.5 mass % or lower, more preferably 14 mass % or lower.

<17> The solid composition as described in any one of <13> to <16> above, which has a content of organic acid (E) of 2 mass % or higher, preferably 2.5 mass % or higher, more preferably 3 mass % or higher, even more preferably 8 mass % or higher, and 18 mass % or lower, preferably 15 mass % or lower, more preferably 12 mass % or lower, even more preferably 11 mass % or lower.

<18> The solid composition as described in any one of <13> to <17> above, which has a content mass ratio of wheat albumin (A) to carbonate salt (D), (A)/(D) of 1.5 or higher, preferably 2.5 or higher, more preferably 2.6 or higher, even more preferably 3.5 or higher, and 16.5 or lower, preferably 15.5 or lower, more preferably 12 or lower, even more preferably 5 or lower.

<19> The solid composition as described in any one of <13> to <18> above, which has a content mass ratio of 0.19 wheat albumin (a) to carbonate salt (D), (a)/(D) of 0.2 or higher, preferably 0.3 or higher, more preferably 0.35 or higher, and 4.1 or lower, preferably 3.8 or lower, more preferably 3 or lower.

<20> The solid composition as described in any one of <13> to <19> above, which has an equivalent ratio of organic acid (E) to carbonate salt (D) of 0.7 or higher, preferably 0.8 or higher, more preferably 0.85 or higher, even more preferably 0.9 or higher, and 1.9 or lower, preferably 1.8 or lower, more preferably 1.2 or lower, even more preferably 1.1 or lower.

<21> The solid composition as described in any one of <1> to <20> above, which is a chewable tablet.

<22> A wheat albumin-masking agent comprising, as an active ingredient, a C6 to C12 sugar alcohol.

<23> A method of masking wheat albumin, the method comprising using a C6 to C12 sugar alcohol as a wheat albumin making agent.

<24> Use of a C6 to C12 sugar alcohol for masking wheat albumin.

<25> Use of a C6 to C12 sugar alcohol as a wheat albumin masking agent.

<26> Use of a C6 to C12 sugar alcohol for producing a wheat albumin masking agent.

<27> The use as described in any one of <24> to <26> above, wherein the C6 to C12 sugar alcohol is at least one species selected from among maltitol, sorbitol, and lactitol, preferably at least one species selected from among maltitol, sorbitol, and lactitol, more preferably maltitol, sorbitol, or a combination thereof, even more preferably maltitol.

EXAMPLES

Raw Material

Wheat albumin: Wheat Albumin NA-1 (product of Nisshin Pharma Inc., 0.19 wheat albumin content: 25%)

[Aspartic Acid Analysis]

A solid composition (50 mg) was dissolved in distilled water (1 g), and the solution was centrifuged by means of a centrifugal separator at 3,000 rpm and 25° C. for 10 minutes. To the thus-recovered supernatant (500 μL), 5% trichloroacetic acid (500 μL) was added, and the mixture was centrifuged by means of a centrifugal separator at 10,000 r/min and 5° C. for 10 minutes. The thus-recovered supernatant (500 μL) was diluted 2- to 10-fold with 0.02N hydrochloric acid, and the dilute was filtered with a 0.2-μm filter, to thereby recover a sample. The sample was analyzed by means of an amino acid analyzer (Hitachi L-8800).

[Carbonate Salt Analysis]

The content of a carbonate salt of a solid composition was determined through the following procedure.

An aliquot (0.1 to 0.2 g) of the solid composition was sampled, and water (10 mL) and 50% phosphoric acid (2 mL) were added to the solid composition sample. The sample was maintained in a tightly sealed container and subjected to ultrasonication for 10 minutes. The sample was allowed to stand for one hour, and a head space gas sample was analyzed through gas chromatography, to thereby determine the $CO_2$ amount. The carbonate salt amount was calculated from the $CO_2$ amount.

<Gas Chromatograph Operational Conditions>
Model: GC-14B [Shimadzu Corporation]
Detector: TCD
Column: Chromosorb 101, 80 to 100 mesh
  Glass tube, φ3.2 mm×2 m
Temperature: 50° C. (column), 100° C. (inlet and detector)
Cell current: 75 mA
Gas pressure: helium (carrier gas), 100 kPa
Injection amount: Head space gas 0.2 mL

[Organic Acid Analysis]

The organic acid of a solid composition was determined through the following procedure.

An aliquot (1 g) of a solid composition was sampled, and 5% perchloric acid (20 mL) was added thereto. The mixture was shaken for 10 minutes for extraction. Water was added to the extract to a total volume of 200 mL, and the diluted extract was ultrasonicated for 10 minutes. The sample was filtered and subsequently analyzed through high-performance liquid chromatography.

<HPLC Operational Conditions>
Model: LC-20AD [Shimadzu Corporation]
Detector: UV-Vis spectrophotometer SPD-20AV [Shimadzu Corporation]
Column temperature: 40° C.
Mobile phase: 3 mmol/L perchloric acid
Reaction liquid: 0.2 mmol/L bromothymol blue-containing 15 mmol/L disodium hydrogenphosphate solution
Flow rate: 1.0 mL/min (mobile phase), 1.4 mL/min (reaction liquid)
Measurement wavelength: 445 nm Chewable Tablet Preparation Examples 1 to 13, and Comparative Examples 1 to 4

Raw materials were mixed together at compositional proportions shown in Table 1. In each case, the mixture was compressed by means of a single punch tableting machine (RIKEN) with a ring-form punch (hole diameter: 13 mm), to thereby produce chewable tablets, each tablet having a weight of 1,000 mg. The contents of 0.19 wheat albumin (a) of the produced chewable tablets are shown in Table 1.

The thus-produced inventive products and comparative products were subjected to sensory evaluation by three expert panelists. An offensive odor intrinsic to wheat albumin during ingestion, and bad odor returning from the gullet during and/or after ingestion of wheat albumin were assessed with the following ratings. In each case, the ratings given by the panelists were averaged. Table 1 shows the results.

[Offensive Odor Intrinsic to Wheat Albumin]
5: No offensive odor
4: Virtually no offensive odor
3: Slight offensive odor
2: Strong offensive odor
1: Very strong offensive odor

[Bad Returning Odor]
5: No bad returning odor
4: Virtually no bad returning odor
3: Slight bad returning odor
2: Strong bad returning odor
1: Very strong bad returning odor

TABLE 1

| | | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|---|
| Composition (mass %) | (A) Wheat albumin*[1] | 50 | 50 | 30 | 40 | 60 | 70 | 50 | 50 | 50 | 30 |
| | (B) Maltitol | 35 | 20 | 55 | 45 | 25 | 15 | — | 20 | — | 10 |
| | (B) Sorbitol | — | — | — | — | — | — | 35 | 15 | — | — |
| | (B) Lactitol monohydrate | — | — | — | — | — | — | — | — | 35 | — |
| | Sucrose | — | — | — | — | — | — | — | — | — | — |
| | Dextrin | — | 15 | — | — | — | — | — | — | — | — |
| | Cornstarch | — | — | — | — | — | — | — | — | — | 45 |
| | Cryst. cellulose | 13 | 13 | 13 | 13 | 13 | 13 | 13 | 13 | 13 | 13 |
| | Ca stearate | 2 | 2 | 2 | 2 | 2 | 2 | 2 | 2 | 2 | 2 |
| | Total | 100.0 | 100.0 | 100.0 | 100.0 | 100.0 | 100.0 | 100.0 | 100.0 | 100.0 | 100.0 |
| (a) 0.19 Wheat albumin (mass %) | | 12.5 | 12.5 | 7.5 | 10 | 15 | 17.5 | 12.5 | 12.5 | 12.5 | 7.5 |
| (B)/(A) | | 0.70 | 0.40 | 1.83 | 1.13 | 0.42 | 0.21 | 0.70 | 0.70 | 0.70 | 0.33 |
| (B)/(a) | | 2.80 | 1.60 | 7.33 | 4.50 | 1.67 | 0.86 | 2.80 | 2.80 | 2.80 | 1.33 |
| Evaluation | Wheat albumin offensive odor | 5 | 4 | 5 | 5 | 4 | 3 | 5 | 5 | 3 | 4 |
| | Bad returning odor | 5 | 5 | 5 | 5 | 4 | 3 | 4 | 4 | 3 | 4 |

| | | Ex. 11 | Ex. 12 | Ex. 13 | Comp. Ex. 1 | Comp. Ex. 2 | Comp. Ex. 3 | Comp. Ex. 4 |
|---|---|---|---|---|---|---|---|---|
| Composition. (mass %) | (A) Wheat albumin*[1] | 30 | 50 | 40 | 50 | 50 | 80 | 50 |
| | (B) Maltitol | 25 | 15 | 30 | 5 | — | 5 | — |
| | (B) Sorbitol | — | — | — | — | — | — | — |
| | (B) Lactitol monohydrate | — | — | — | — | — | — | — |
| | Sucrose | — | — | — | — | 35 | — | — |

TABLE 1-continued

|  | | | | | | | | |
|---|---|---|---|---|---|---|---|---|
|  | Dextrin | — | — | — | 30 | — | — | 35 |
|  | Cornstarch | 30 | 20 | 15 | — | — | — | — |
|  | Cryst. cellulose | 13 | 13 | 13 | 13 | 13 | 13 | 13 |
|  | Ca stearate | 2 | 2 | 2 | 2 | 2 | 2 | 2 |
|  | Total | 100.0 | 100.0 | 100.0 | 100.0 | 100.0 | 100.0 | 100.0 |
| (a) 0.19 Wheat albumin (mass %) | | 7.5 | 12.5 | 10 | 12.5 | 12.5 | 20 | 12.5 |
| (B)/(A) | | 0.83 | 0.30 | 0.75 | 0.10 | — | 0.06 | — |
| (B)/(a) | | 3.33 | 1.20 | 3.00 | 0.40 | — | 0.25 | — |
| Evaluation | Wheat albumin offensive odor | 5 | 4 | 5 | 2 | 2 | 1 | 1 |
|  | Bad returning odor | 5 | 3 | 4 | 2 | 2 | 1 | 1 |

*[1]Wheat Albumin NA-1 (product of Nisshin Pharma Inc.)

As is clear from Table 1, the inventive products of the present invention were found to provide reduced offensive odor intrinsic to wheat albumin and reduced bad returning odor attributed to wheat albumin, as compared with comparative products. In Comparative Example 4 (containing no C6 to C12 sugar alcohol), in Comparative Examples 1 and 3 (low content of C6 to C12 sugar alcohol), and in Comparative Example 2 (containing sucrose), the offensive odor intrinsic to wheat albumin and bad returning odor attributed to wheat albumin were strong.

Preparation of Chewable Tablets

Examples 14 to 21

Chewable tablets were obtained in a manner similar to that of Example 1, except that raw materials having the compositional proportions shown in Table 2 were mixed. The contents of 0.19 wheat albumin (a) of the produced chewable tablets are shown in Table 2.

The thus-produced inventive products of the present invention were sensory evaluated by three expert panelists. "An offensive odor intrinsic to wheat albumin during ingestion," and "bad returning odor returning from the gullet during and/or after ingestion of wheat albumin" were assessed with the aforementioned ratings. Also, "a bad taste intrinsic to wheat albumin," "a taste derived from added amino acid," "adhesion in the mouth during ingestion," "bubbly mouth feel," and "balance in taste and flavor" were assessed with the following ratings. In each case, the ratings given by the panelists were averaged. Table 2 shows the results.
[Bad Taste Intrinsic to Wheat Albumin]
5: No bad taste
4: Virtually no bad taste
3: Slight bad taste
2: Strong bad taste
1: Very strong bad taste
[Taste Derived from Added Amino Acid]
5: No taste derived from added amino acid, satisfactory taste and flavor
4: Virtually no taste derived from added amino acid
3: Slight taste derived from added amino acid
2: Strong taste derived from added amino acid
1: Very strong taste derived from added amino acid
[Adhesion in the Mouth]
5: Very little adhesion to teeth and tongue
4: Little adhesion to teeth and tongue
3: Slightly strong adhesion to teeth and tongue
2: Strong adhesion to teeth and tongue
1: Very strong adhesion to teeth and tongue
[Bubbly Mouth Feel]
5: Very good bubble breakage in mouth
4: Good bubble breakage in mouth
3: Slightly good bubble breakage in mouth
2: Poor bubble breakage in mouth
1: Very poor bubble breakage in mouth
[Balance in Taste and Flavor]
5: Very well-balanced taste and flavor, without prominent tastes and flavors of organic acid and carbonate salt
4: Well-balanced taste and flavor, without prominent tastes and flavors of organic acid and carbonate salt
3: Slightly well-balanced taste, without prominent tastes and flavors of organic acid and carbonate salt
2: Poorly-balanced taste and flavor, without prominent tastes and flavors of organic acid and carbonate salt
1: Very poorly-balanced taste and flavor, without prominent tastes and flavors of organic acid and carbonate salt

TABLE 2

|  |  | Ex. 14 | Ex. 15 | Ex. 16 | Ex. 17 | Ex. 18 | Ex. 19 | Ex. 20 | Ex. 21 |
|---|---|---|---|---|---|---|---|---|---|
| Composition (mass %) | (A) Wheat albumin*[1] | 40 | 40 | 40 | 40 | 40 | 35 | 40 | 40 |
|  | (B) Maltitol | 30 | 30 | 30 | 30 | 30 | 27 | 30 | 30 |
|  | (C) Na aspartate monohydrate | — | 0.01 | 0.005 | 0.02 | — | — | — | 0.01 |
|  | (D) Na hydrogencarbonate | — | — | — | — | 4 | 13 | 9 | 9 |
|  | (E) Citric acid | — | — | — | — | 3 | 10 | 7 | 7 |
|  | Cornstarch | 15 | 14.99 | 14.995 | 14.98 | 8 | — | — | — |
|  | Cryst. cellulose | 13 | 13 | 13 | 13 | 13 | 13 | 12 | 11.99 |
|  | Ca stearate | 2 | 2 | 2 | 2 | 2 | 2 | 2 | 2 |
|  | Total | 100.0 | 100.0 | 100.0 | 100.0 | 100.0 | 100.0 | 100.0 | 100.0 |
| (a) 0.19 Wheat albumin (mass %) | | 10.0 | 10.0 | 10.0 | 10.0 | 10.0 | 8.8 | 10.0 | 10.0 |
| (B)/(A) | | 0.75 | 0.75 | 0.75 | 0.75 | 0.75 | 0.77 | 0.75 | 0.75 |
| (B)/(a) | | 3.00 | 3.00 | 3.00 | 3.00 | 3.00 | 3.09 | 3.00 | 3.00 |
| (c) Aspartic acid amount (mass %) | | — | 0.016 | 0.012 | 0.023 | — | — | — | 0.016 |
| (a)/(c) | | — | 635 | 842 | 426 | — | — | — | 635 |
| (A)/(D) content mass ratio | | — | — | — | — | 10.00 | 2.69 | 4.44 | 4.44 |

TABLE 2-continued

|  | Ex. 14 | Ex. 15 | Ex. 16 | Ex. 17 | Ex. 18 | Ex. 19 | Ex. 20 | Ex. 21 |
|---|---|---|---|---|---|---|---|---|
| (a)/(D) content mass ratio | — | — | — | — | 2.50 | 0.67 | 1.11 | 1.11 |
| Eq. ratio of (E) to (D) | — | — | — | — | 0.98 | 1.01 | 1.02 | 1.02 |
| Evaluation Wheat albumin offensive odor | 5 | 5 | 5 | 5 | 5 | 5 | 5 | 5 |
| Bad returning odor | 4 | 4 | 4 | 4 | 4 | 4 | 4 | 4 |
| Wheat albumin bad taste | 2 | 5 | 3 | 5 | 4 | 5 | 4 | 5 |
| Added amino acid taste | — | 5 | 5 | 3 | — | — | — | 5 |
| Adhesion in mouth | 2 | 2 | 2 | 2 | 4 | 5 | 5 | 5 |
| Bubbly mouse feel | — | — | — | — | 5 | 5 | 5 | 5 |
| Balance in taste and flavor | — | — | — | — | 4 | 5 | 5 | 5 |

*[1] Wheat Albumin NA-1 (product of Nisshin Pharma Inc.)

As is clear from Table 2, in Examples 15 to 17, and 21, further employing an aspartate salt, the bad taste intrinsic to wheat albumin was found to be reduced, and a taste derived from added amino acid was not detected, attaining a favorable taste and flavor. In Examples 18 to 21 further employing a carbonate salt and an organic acid, stickiness and adhesion in the mouth during ingestion were suppressed, and a favorable bubbly mouse feel and a well-balanced taste and flavor were provided.

The invention claimed is:

1. A solid composition comprising ingredients (A) and (B):
   (A) wheat albumin, and
   (B) maltitol, sorbitol, lactitol, or any combination thereof,
   wherein a content mass ratio of the ingredient (B) to the ingredient (A) is from 0.2 to 1.9,
   wherein a content of the maltitol, sorbitol, lactitol, or combination thereof (B) is from 10 to 55 mass %, and
   wherein a content of the wheat albumin (A) is 30 mass % or higher and 70 mass % or lower.

2. The solid composition according to claim 1, wherein (B) is maltitol.

3. The solid composition according to claim 1,
   wherein the wheat albumin (A) comprises 0.19 wheat albumin (a), and
   a content of the 0.19 wheat albumin (a) in the wheat albumin (A) is 10 mass % or higher and 60 mass % or lower.

4. The solid composition according to claim 1, wherein the content of the wheat albumin (A) is 30 mass % or higher and 55 mass % or lower.

5. The solid composition according to claim 4, wherein a content of (B) is 30 mass % or higher and 55 mass % or lower.

6. The solid composition according to claim 1, wherein the content mass ratio of the ingredient (B) to the ingredient (A) is 0.5 to 1.9.

7. The solid composition according to claim 1, further comprising an aspartic acid or a salt thereof (C),
   wherein the wheat albumin (A) comprises 0.19 wheat albumin (a) and
   wherein the solid composition has a content mass ratio of 0.19 wheat albumin (a) to aspartic acid or a salt thereof (C) of 10 or higher and 1,000 or lower in terms of aspartic acids.

8. The solid composition according to claim 1, which further comprises a carbonate salt (D) and an organic acid (E) and has a content mass ratio of wheat albumin (A) to carbonate salt (D) of 1.5 or higher and 16.5 or lower and an equivalent ratio of organic acid (E) to carbonate salt (D) of 0.7 or higher and 1.9 or lower.

9. The solid composition according to claim 1, which is in the form of a chewable tablet.

10. A solid composition comprising ingredients (a) and (B):
    (a) 0.19 wheat albumin, and
    (B) maltitol, sorbitol, lactitol, or any combination thereof,
    wherein a content mass ratio of the ingredient (B) to the ingredient (a) is 0.8 or higher,
    wherein a content of the maltitol, sorbitol, lactitol, or combination thereof (B) is from 10 to 55 mass %, and
    wherein a total wheat albumin content in the solid composition is 30 mass % or higher and 70 mass % or lower.

11. The solid composition according to claim 10, wherein (B) is maltitol.

12. The solid composition according to claim 10, wherein a content of 0.19 wheat albumin (a) is 6 mass % or higher and 18 mass % or lower.

13. The solid composition according to claim 10, wherein a content of the 0.19 wheat albumin (a) is 7.5 mass % or higher and 13 mass % or lower.

14. The solid composition according to claim 13, wherein a content of (B) is 30 mass % or higher and 55 mass % or lower.

15. The solid composition according to claim 10, wherein the content mass ratio of the ingredient (B) to the ingredient (a) is 1.5 or higher and 7.5 or lower.

16. A method of masking an odor of wheat albumin, the method comprising:
    including, in a composition in need thereof, an effective amount of a C6 to C12 sugar alcohol,
    wherein the composition comprises wheat albumin.

* * * * *